(12) United States Patent
Fukamizu et al.

(10) Patent No.: US 7,667,856 B2
(45) Date of Patent: Feb. 23, 2010

(54) OPTICAL CHARACTERISTIC MEASURING APPARATUS

(75) Inventors: Tomohiro Fukamizu, Sakai (JP);
Yoshiyuki Nagashima, Sakai (JP);
Katsutoshi Tsurutani, Osaka (JP);
Shinji Shimizu, Sakai (JP)

(73) Assignee: Konica Minolta Sensing, Inc., Osaka (JP)

( * ) Notice: Subject to any disclaimer, the term of this patent is extended or adjusted under 35 U.S.C. 154(b) by 0 days.

(21) Appl. No.: 12/284,432

(22) Filed: Sep. 22, 2008

(65) Prior Publication Data
US 2009/0079984 A1    Mar. 26, 2009

(30) Foreign Application Priority Data
Sep. 26, 2007    (JP) ............................. 2007-250052

(51) Int. Cl.
*G01B 11/14*    (2006.01)
*G01H 1/00*    (2006.01)

(52) U.S. Cl. ...................... 356/614; 356/601; 73/653

(58) Field of Classification Search ................. 356/601, 356/614; 73/570, 653
See application file for complete search history.

(56) References Cited

U.S. PATENT DOCUMENTS 5,394,233  A  *  2/1995  Wang .................. 356/5.01
7,262,854  B2     8/2007  Imura

FOREIGN PATENT DOCUMENTS

JP    2006-10508    1/2006

* cited by examiner

*Primary Examiner*—Roy Punnoose
(74) *Attorney, Agent, or Firm*—Brinks Hofer Gilson & Lione (57) ABSTRACT

An optical characteristic measuring apparatus of the invention is configured in such a manner that a specular reflection light component in reflection light from an object to be measured is received, and shake of the apparatus is detected based on the amount of the received light. The optical characteristic measuring apparatus having the above arrangement enables to precisely measure an optical characteristic of the object to be measured, without the need of providing a mechanical switch or a like device, and without depending on the shape of the object to be measured.

5 Claims, 6 Drawing Sheets

OPTICAL CHARACTERISTIC MEASURING APPARATUS

This application is based on Japanese Patent Application No. 2007-250052 filed on Sep. 26, 2007, the contents of which are hereby incorporated by reference.

BACKGROUND OF THE INVENTION

1. Field of the Invention

The present invention relates to an optical characteristic measuring apparatus for measuring an optical characteristic of a special effect coating such as a metallic coating or a pearlescent coating having different hues depending on an illuminating direction or an observing direction.

2. Description of the Related Art

Conventionally, a metallic coating or a pearlescent coating to be used as e.g. a coating of an automobile body contains a luster material composed of aluminum flakes, mica flakes, or a like substance. An intensity of reflection light from the luster material is different depending on an observing direction because of a variation in reflection light resulting from a variation in orientations of the luster material. This enables to obtain a metallic effect or a pearlescent effect. In the case where an optical characteristic of a material such as a metallic coating or a pearlescent coating having the above property is measured, it is impossible to evaluate a difference in optical characteristic resulting from a variation in orientations of the luster material merely by measuring reflection light in one angular direction. Accordingly, normally, the difference in optical characteristic is evaluated by measuring reflection light in multiple angular directions. Heretofore, there has been used a multi-angle colorimeter provided with a multi-angle geometry of illuminating in multiple directions and receiving in a single direction, or illuminating in a single direction and receiving in multiple directions, as an optical characteristic measuring apparatus capable of measuring reflection light in different angular directions (see e.g. Japanese Unexamined Patent Publication No. 2006-10508). Generally, a portable or handy multi-angle calorimeter is desirable to allow an operator to perform measurement at various different measurement positions e.g. in performing measurement with respect to a surface of an automobile body, as described above.

In the case where measurement is performed by the multi-angle calorimeter, illumination in multiple directions or receiving in multiple directions is carried out during a measuring operation. This may require a relatively long measurement time. If the multi-angle colorimeter is a handy type apparatus, it is highly likely that shake or a like movement of the apparatus may occur during the measuring operation. The shake during the measuring operation is a primary cause of degrading measurement reproducibility by the multi-angle colorimeter.

In order to solve the above drawback, the following approach has been proposed. Specifically, a mechanical switch operable to be turned on and off depending on the distance between a sample and the measuring apparatus is provided near a measurement aperture portion. The operator is allowed to detect whether the measuring apparatus is tilted relative to the sample, or displaced from an intended position by monitoring a change of the mechanical switch between on and off states during a measuring operation.

In the above approach, judgment is made based on binary data by turning on and off the mechanical switch. This may require the switch to be operated for threshold value adjustment or sensitivity adjustment at the time of producing the measuring apparatus or in use of the measuring apparatus. Also, the entire part of the mechanical switch is required to be firmly contacted with a sample surface, in view of a point that the switch has a mechanical structure. Accordingly, the mechanical switch is not suitable in measuring an object to be measured having many curved portions such as a surface of an automobile body. Specifically, in the conventional measuring apparatus, positions to be measured are limited to flat plane portions. In the above arrangement, it is often the case that the operator is forced to perform measurement at a position other than a position where the operator intends to perform measurement, e.g. a position where the mechanical switch is firmly contacted with the sample surface, and the mechanical switch is allowed to be depressed.

SUMMARY OF THE INVENTION

In view of the above conventional examples, it is an object of the present invention to provide an optical characteristic measuring apparatus that enables to precisely measure an optical characteristic of an object to be measured including a curved surface, without the need of providing a mechanical switch or a like device, and without depending on the shape of the object to be measured.

An optical characteristic measuring apparatus according to an aspect of the invention is configured in such a manner that a specular reflection light component in reflection light from an object to be measured is received, and shake of the apparatus is detected based on the amount of the received light. The optical characteristic measuring apparatus having the above arrangement enables to precisely measure an optical characteristic of the object to be measured, without the need of providing a mechanical switch or a like device, and without depending on the shape of the object to be measured.

These and other objects, features and advantages of the present invention will become more apparent upon reading the following detailed description along with the accompanying drawings.

BRIEF DESCRIPTION OF THE DRAWINGS

FIGS. 7A and 7B are diagrams showing an intensity distribution of reflection light to be reflected on a measurement surface of an object to be measured in the case where the measurement surface of the object to be measured is illuminated by a light source, in terms of a distance from an aperture center, wherein FIG. 7A shows a case that an aperture plane of the measurement aperture is substantially in agreement with the measurement surface of the object to be measured, and FIG. 7B shows a case that the aperture plane of the measurement aperture is not in agreement with the measurement surface of the object to be measured.

DETAILED DESCRIPTION OF THE PREFERRED EMBODIMENTS OF THE INVENTION

Figure 1:
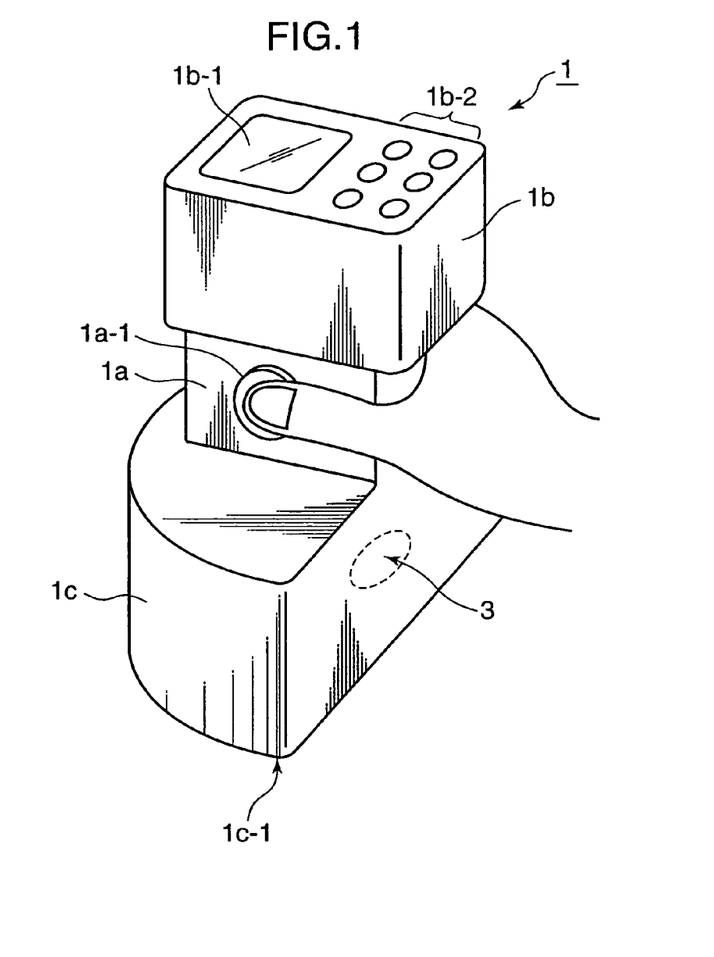
FIG. 1 is a diagram showing an external appearance of a multi-angle calorimeter embodying the invention.

A multi-angle calorimeter embodying the invention is described. FIG. 1 is a diagram showing an external appearance of the multi-angle colorimeter in accordance with the embodiment of the invention. As shown in FIG. 1, the multi-angle colorimeter 1 includes a holding portion 1a to be held by an operator, an operation display portion 1b formed at one end of the holding portion 1a, and a contact portion 1c formed at the opposite end of the holding portion 1a. The multi-angle colorimeter 1 is a handy apparatus with excellent portability i.e. has a portable structure to be carried by the operator.

The holding portion 1a has a measurement trigger button 1a-1 for allowing an operator to input a command to start a measuring operation with respect to an object to be measured i.e. a sample. The measurement trigger button 1a-1 is arranged at such a position that the thumb of an operator's hand is allowed to be contacted when the operator holds the holding portion 1a, considering operability of inputting a command to start the measuring operation. The operation display portion 1b includes a display portion 1b-1 for displaying a measurement result, and an operation portion 1b-2 constituted of a power source button for switching on and off the power source of the measuring apparatus, a display switching button for switching on and off a display operation to be performed by the display portion 1b-1, and the like. The contact portion 1c is a member having a bottom surface 1c-1 to be contacted with a measurement surface i.e. a sample surface of the object to be measured. A measurement aperture 3 is formed in the bottom surface 1c-1.

Figure 2:
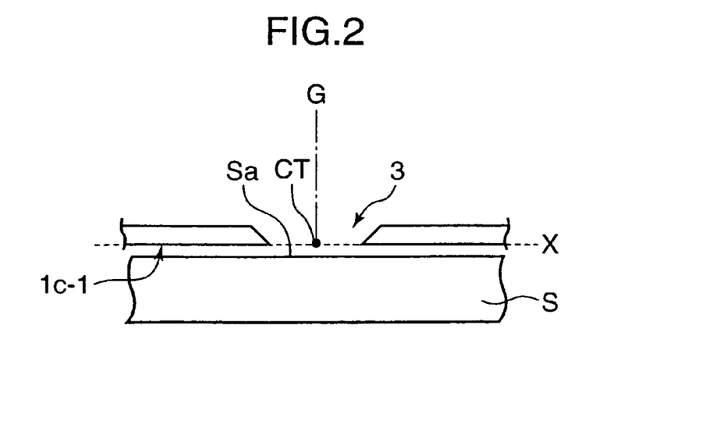
FIG. 2 is a cross-sectional view showing an arrangement of a portion near a measurement aperture of the multi-angle calorimeter.

FIG. 2 is a cross-sectional view showing an arrangement of a portion near the measurement aperture 3. As shown in FIG. 2, the bottom surface 1c-1 of the contact portion 1c is a flat plane. The measurement aperture 3 as a measurement aperture portion is formed in the flat plane, and has e.g. an elliptical shape. Hereinafter, the flat plane is called as an aperture plane X, the center of the measurement aperture 3 is called as an aperture center CT, and a straight line perpendicularly intersecting with the aperture plane X and passing the aperture center CT is called as a normal G. In FIG. 2, the bottom surface 1c-1 of the contact portion 1c and the measurement surface of the object S to be measured are shown to be away from each other to clearly illustrate the aperture plane X. However, in an actual apparatus, in the case where the measurement surface Sa of the object S to be measured is a uniform flat plane, the bottom surface 1c-1 of the contact portion 1c is firmly contacted with the measurement surface Sa of the object S to be measured.

Figure 3:
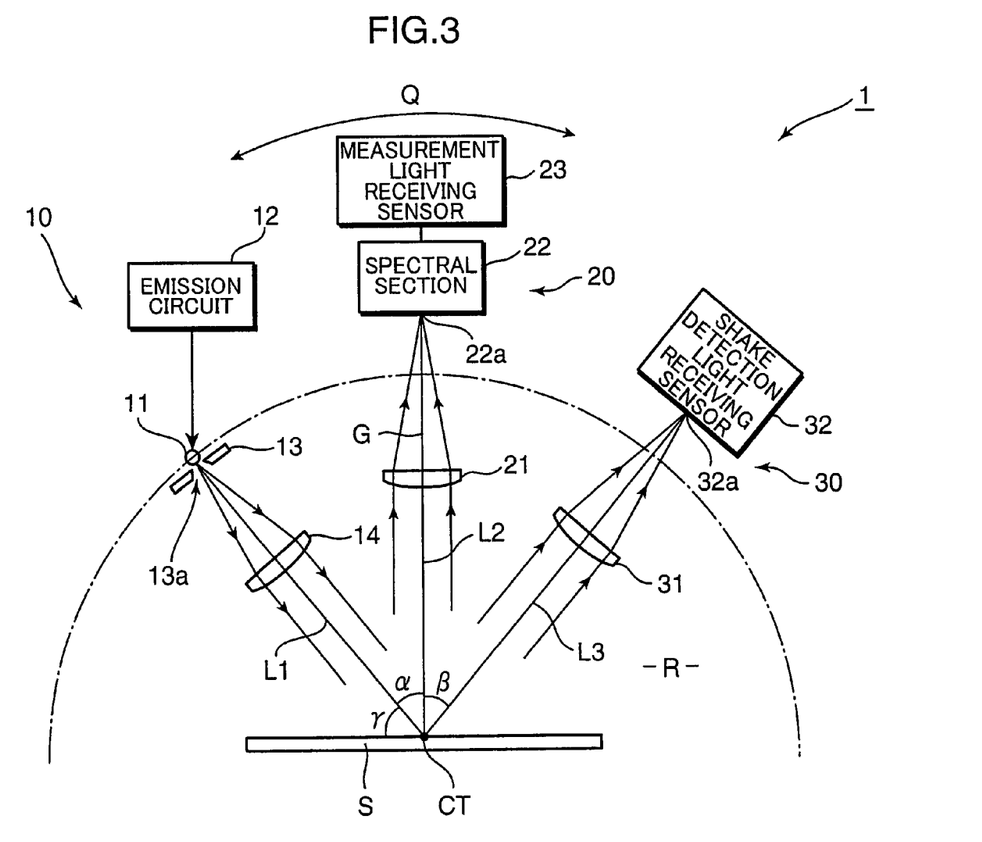
FIG. 3 is a diagram showing an example of an internal arrangement of the multi-angle colorimeter.
Figure 4:
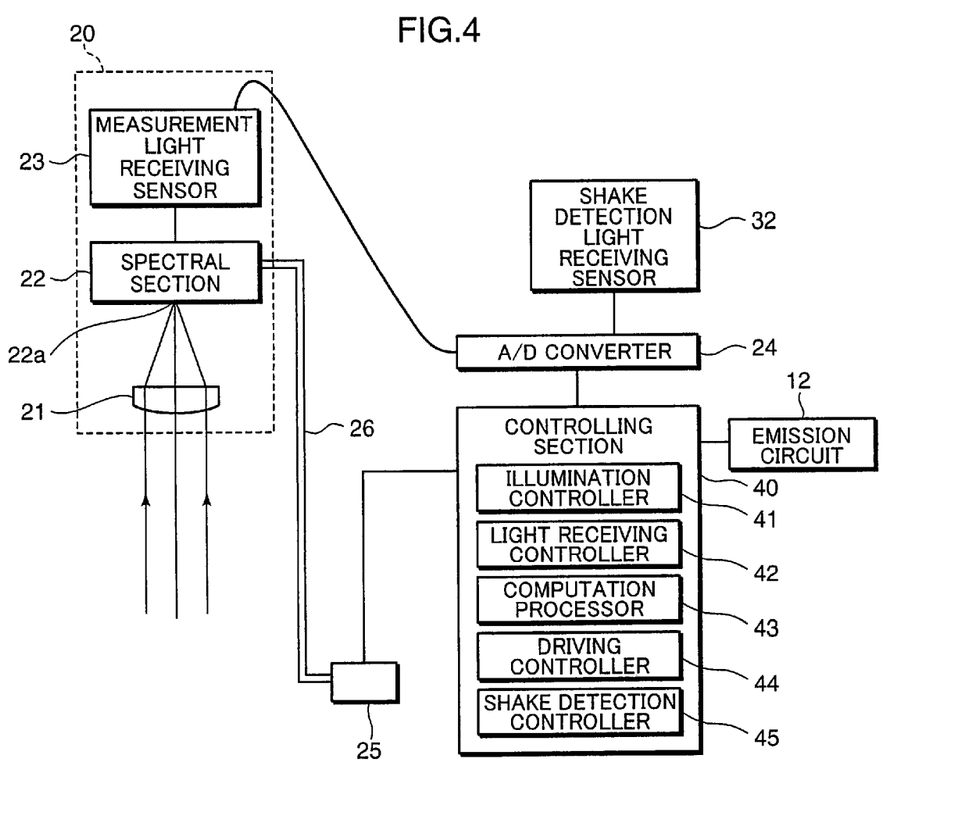
FIG. 4 is a block diagram showing a control system of the multi-angle calorimeter.

FIG. 3 is a diagram showing an example of an internal arrangement of the multi-angle calorimeter 1. FIG. 4 is a block diagram showing a control system of the multi-angle colorimeter 1. As shown in FIG. 3, the multi-angle calorimeter 1 includes an illuminating section 10, a light receiving section 20, a shake detecting section 30, and a controlling section 40. The illuminating section 10 has a light source 11 constituted of a halogen lamp, an LED (light emitting diode), or a like device, an emission circuit 12 for driving the light source 11, a light flux defining plate 13 for defining a light flux to be outputted from the light source 11, and a collimator lens 14. The light source 11 is fixed at a position with a predetermined angle (in this embodiment, 45°) with respect to the normal G to the measurement surface Sa of the object S to be measured. The light flux defining plate 13 is arranged at such a position that an aperture 13a thereof is in agreement with a focal position of the collimator lens 14. A light flux from the light source 11 that has passed through the aperture 13a of the light flux defining plate 13 is collimated by the collimator lens 14 into a parallel light flux, and the parallel light flux is guided to the measurement surface Sa of the object S to be measured. The illuminating section 10 illuminates a measurement area of the measurement surface Sa on the object S to be measured at a predetermined angle within a measurement geometric plane to be described later.

The light receiving section 20 has a light receiving optical system 21 for condensing the parallel light flux reflected on the object S to be measured; a spectral section 22 provided with an incident slit 22a, to be described later, for limiting the light transmitted through the light receiving optical system 21, and a diffraction grating 22c, to be described later, for separating an incident light flux depending on each wavelength; and a measurement light receiving sensor 23 for outputting spectral data depending on a light intensity. The light receiving section 20 is adapted to measure a spectral intensity of a light flux which has been transmitted through the light receiving optical system 21 and incident through the incident slit 22a. The light receiving section 20 is pivotally rotatable in the directions of the arrows Q in FIG. 3, which will be described later.

Figure 5:
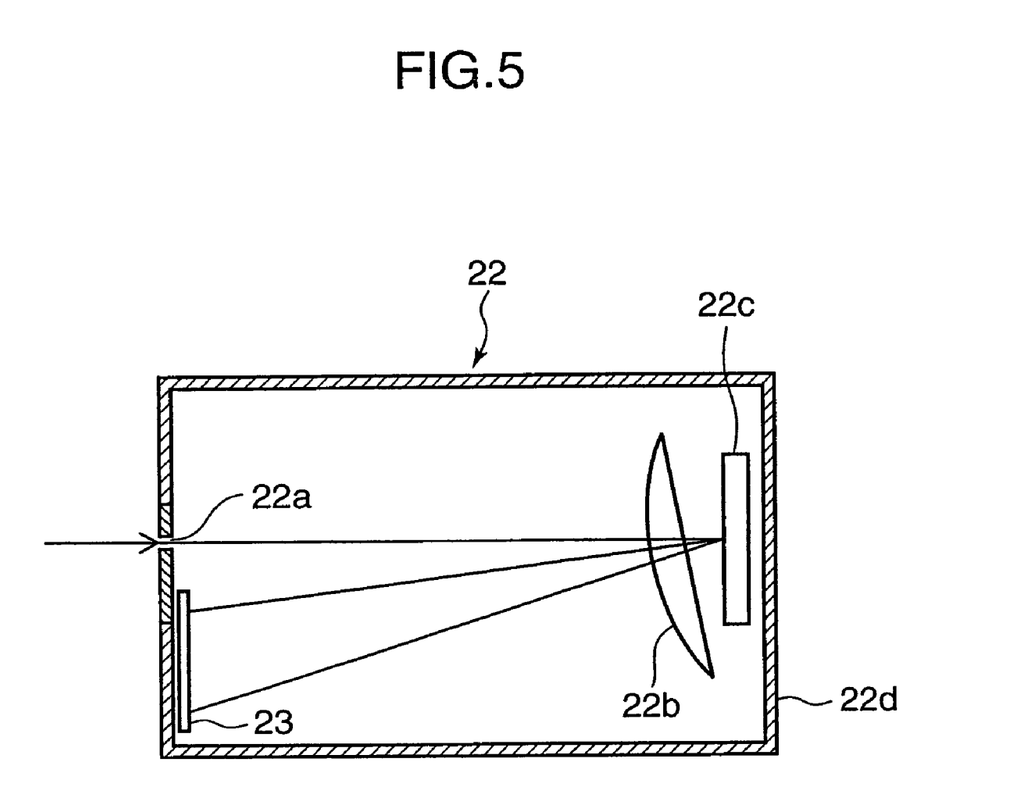
FIG. 5 is a schematic diagram showing an example of a spectral section in the multi-angle colorimeter.

FIG. 5 is a schematic diagram showing an example of the spectral section 22. As shown in FIG. 5, the spectral section 22 has a casing 22d formed with the incident slit 22a at an appropriate position, a lens 22b, and the diffraction grating 22c which are provided inside the casing 22d. The lens 22b is adapted to guide light to be measured which has passed through the incident slit 22a to the diffraction grating 22c as parallel light, and forms a dispersed image of the incident slit 22a which has been dispersed by the diffraction grating 22c on a light receiving surface of the measurement light receiving sensor 23. The diffraction grating 22c has a function of reflecting and dispersing incident light to be measured depending on each wavelength, and forms the dispersed image of the incident slit 22a on the light receiving surface of the measurement light receiving sensor 23.

The measurement light receiving sensor 23 has multiple light receiving channels i.e. pixels arranged at a predetermined interval. For instance, the measurement light receiving sensor 23 is constituted of a silicon photodiode array, wherein a predetermined number of silicon photodiodes are arranged in a row in one direction. Dispersed light, i.e. a dispersed image of the incident slit, which has been incident on each of the light receiving channels of the measurement light receiving sensor 23, is converted into an electric current by a photoelectric conversion operation of each of the photodiodes for outputting to an A/D converter 24 to be described later.

The shake detecting section 30 includes a light receiving optical system 31 for condensing a parallel light flux reflected on the object S to be measured; and a shake detection light receiving sensor 32, arranged at an image forming position of the light receiving optical system 31, for outputting data depending on a light amount i.e. a light intensity of a light flux incident from an incident slit 32a for limiting the light transmitted through the light receiving optical system 31. The shake detecting section 30 is adapted to detect a light amount (i.e. a variation in light amount or a time-based change in light amount) of a specular reflection light component so as to detect whether shake or a like movement has occurred during a measuring operation, in other words, detect whether the multi-angle colorimeter 1 is tilted with respect to the measurement surface Sa of the object S to be measured in the directions of the arrows Q in FIG. 3. In other words, the shake detecting section 30 monitors a variation in reflection light.

The shake detecting section 30 is fixed at a position in specular reflection direction (including a position in the vicinity of the specular reflection direction) corresponding to a specular reflection angle with respect to an illumination angle α (or an irradiation angle γ) to be defined by the illuminating section 10 as an illuminating system. The shake detecting section 30 is fixed at a position in light receiving direction capable of obtaining a reflection angle β (i.e. the angle defined by the normal G to an incident point, and a reflection light ray, which is an angle within a plane including an incident angle α, and is equal to the incident angle α) with respect to the incident angle α (i.e. the angle defined by an incident light ray and the normal G). In other words, the shake detecting section 30 is arranged at a position capable of acquiring i.e. receiving a specular reflection light component i.e. specular reflection light to be described later. The position in specular reflection direction in the specification does not strictly indicate a position in specular reflection direction corresponding to a specular reflection angle, but indicates a position within a predetermined area including a position corresponding to the specular reflection direction, e.g., a position expressed by an angular range of ±5° with respect to the specular reflection direction. In summary, a certain range of displacement is allowed, as far as the shake detecting section 30 is arranged at a position capable of receiving a specular reflection light component.

Alternatively, the shake detecting section 30 may have a light flux defining aperture for exclusively passing a specular reflection light component, in place of the light receiving optical system 31. Further alternatively, the shake detecting section 30 may have an optical fiber at a specular reflection position to guide specular reflection light to the shake detection light receiving sensor 32. The shake detecting section 30 is an example of a shake detection light receiving section, and the shake detection light receiving sensor 32 is an example of a light receiving sensor of the shake detection light receiving section.

Similarly to the measurement light receiving sensor 23, the shake detection light receiving sensor 32 is constituted of silicon photodiodes. The shake detection light receiving sensor 32 is operable to convert the specular reflection light into an electric current by a photoelectric conversion operation of each of the photodiodes for outputting to the A/D converter 24 to be described later.

Referring back to FIGS. 3 and 4, an analog light receiving signal to be outputted from each of the light receiving channels of the measurement light receiving sensor 23, and each of the light receiving channels of the shake detection light receiving sensor 32 is subjected to an amplification process by an unillustrated amplifying circuit and an A/D conversion process by the A/D converter 24, and thereafter, the processed signals are outputted to the controlling section 40. In response to output of the processed signal from the measurement light receiving sensor 23, the controlling section 40 calculates a spectral intensity of the light to be measured, and a reflection characteristic value based on the spectral intensity. In response to output of the processed signal from the shake detection light receiving sensor 32, the controlling section 40 calculates a variation in light amount i.e. a change in light amount.

In this embodiment, the light receiving section 20 is connected to an arm member 26 i.e. a connecting member, as an example of a driving force transmitting member for receiving a driving force from a motor 25. As shown in FIG. 4, the light receiving section 20 is a unit constructed by integrally assembling the light receiving optical system 21, the spectral section 22, and the measurement light receiving sensor 23. In response to receiving a driving force from the motor 25 by the arm member 26, the light receiving section 20 is pivotally rotated in the directions of the arrows Q shown in FIG. 3 about an axis which is orthogonal to a plane R (i.e. the plane of FIG. 3, hereinafter, called as a "measurement geometric plane") including an optical axis L1 of incident light to be incident onto the object S to be measured, and an optical axis L2 or L3 of reflection light to be reflected on the object S to be measured, and which passes an intersect (i.e. the aperture center CT) of the optical axis L1 of incident light and the optical axis L2 (or L3) of reflection light. In this arrangement, the light receiving section 20 is operable to change the light receiving position of reflection light, and receive the reflection light at multiple light receiving positions. The light receiving position is defined by a light receiving angle. The light receiving angle is an angle defined by the normal G and the optical axis L2 of the light receiving optical system 21 in the light receiving section 20. In the arrangement of FIG. 3, the light receiving section 20 is aligned with the position of the normal G, where the light receiving angle is zero.

The controlling section 40 is constituted of e.g. a CPU (Central Processing Unit); and a storage section such as an ROM (Read Only Memory) for storing a program for defining an operation of the CPU, and an RAM for temporarily saving data. The controlling section 40 controls overall operations of the multi-angle colorimeter 1. The controlling section 40 functionally includes an illumination controller 41, a light receiving controller 42, a computation processor 43, a driving controller 44, and a shake detection controller 45. The illumination controller 41 controls an emission operation (i.e. turning on and off) of the light source 11 by controlling driving of the emission circuit 12. The driving controller 44 controls driving of the motor 25 i.e. rotation driving of the light receiving section 20 to change the light receiving position. The light receiving controller 42 controls a light receiving operation of the measurement light receiving sensor 23. The shake detection controller 45 controls a light receiving operation of the shake detection light receiving sensor 32.

The computation controller 43 performs a computation process i.e. a reflection characteristic value calculating process of obtaining a reflection characteristic value of the object S to be measured, based on an output signal from the measurement light receiving sensor 23. The computation processor 43 also performs a computation process i.e. a variation amount calculating process of obtaining a time-based variation in the specular reflection light i.e. a time-based change in the light amount of the specular reflection light or a variation amount in the light amount, based on an output signal from the shake detection light receiving sensor 32; and performs a judging process of judging whether the variation amount in the light amount is smaller than a predetermined threshold value. More specifically, the variation amount calculating process to be performed by the computation processor 43 comprises: sequentially reading out light receiving information (also called as a shake detection light receiving value) from the shake detection light receiving sensor 32 a certain number of times e.g. at a predetermined time interval during e.g. a measuring operation when the light receiving section 20 receives reflection light while pivotally rotating with its light receiving position being changed with time; successively comparing e.g. a shake detection light receiving value obtained by the first readout operation with shake detection light receiving values obtained by the succeeding readout operations e.g. by performing a difference operation to calculate the difference.

The computation processor 43 successively compares the difference with a predetermined threshold value predefined in the judging process, and performs an error correcting process if it is judged that the difference is equal to or larger than the threshold value. More specifically, when the error correcting process is started, for instance, the computation processor 43 outputs, to the respective parts of the multi-angle colorimeter 1, a command signal requesting a measuring operation again, and performs a process (called as a re-measuring process) of causing the multi-angle colorimeter 1 to perform a measuring operation again i.e. an operation of receiving reflection light by the light receiving section 20 while changing the light receiving position. In performing the above operation, the computation processor 43 may cause the display portion 1*b*-1 or a like portion to display an error message e.g. indicating that the measuring operation has failed due to shake of the apparatus. Further alternatively, the computation processor 43 may be configured in such a manner that an error message is displayed without performing a re-measuring process to prompt the operator to perform a measuring operation again by depressing the measurement start button or a like member. The threshold value is set to a value i.e. a shake allowable amount that allows a measurement value to have intended measurement precision or fall within an allowable error range. Alternatively, the computation processor 43 may store threshold values of different kinds in advance, as threshold value information, and may be operable to switch to an appropriate threshold value in response to user's designation or a like operation, each time a measuring operation is performed.

Figure 7A:
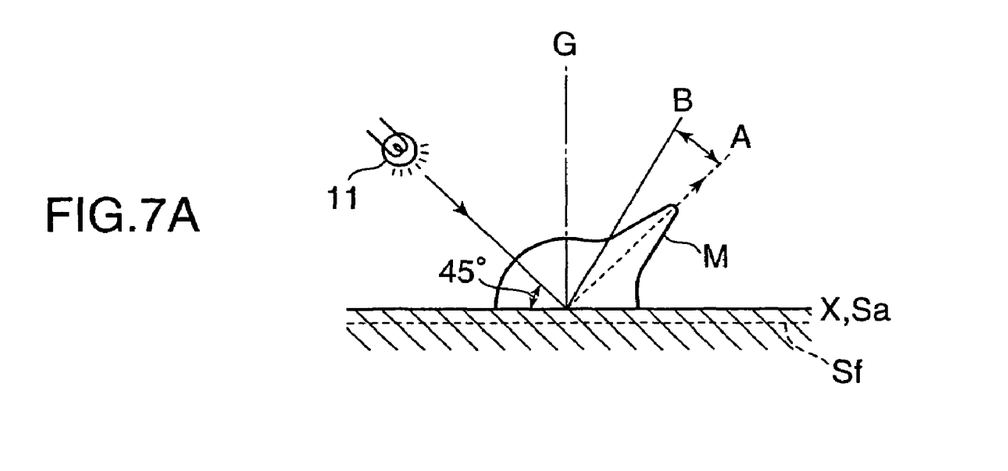
Figure 7B:
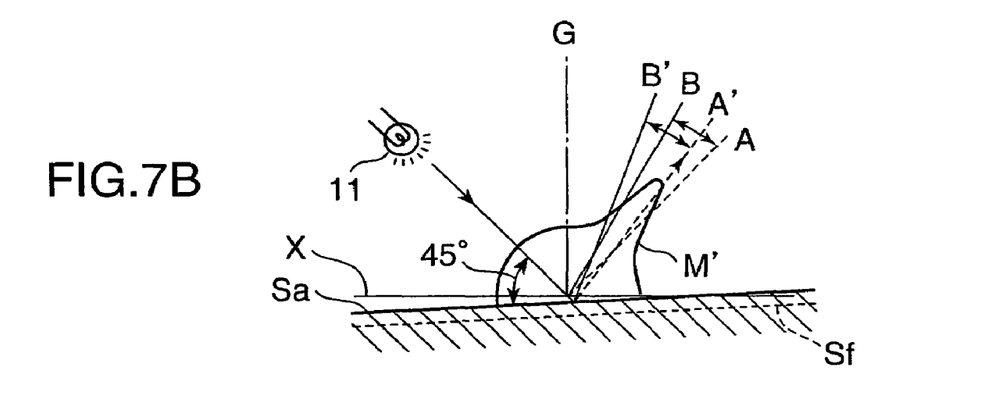

The multi-angle calorimeter 1 in the embodiment has a primary feature that whether shake or a like movement has occurred is detected or judged by detecting a time-based variation in the specular reflection light i.e. a time-based variation in the output from the shake detection light receiving sensor 32. In this section, description is made as to how a variation in specular reflection light is generated in the case where shake has occurred. FIGS. 7A and 7B are diagrams showing an intensity distribution of reflection light to be reflected on the measurement surface Sa of the object S to be measured in the case where the measurement surface Sa of the object S to be measured is illuminated by the light source 11, in terms of a distance from the aperture center CT. Observing intensity distributions M and M' shown in FIGS. 7A and 7B, a protruding portion indicates specular refection light i.e. a specular reflection light component, and the other portion indicates diffused light. As shown in FIG. 7A, in the case where the aperture plane X of the measurement aperture 3 in the multi-angle colorimeter 1 is substantially in agreement with the measurement surface Sa of the object S to be measured, an expected position for receiving specular reflection light is coincident with the actual position for receiving specular reflection light. Accordingly, as shown by the intensity distribution M in FIG. 7A, it is possible to presume that a peak value resides at the expected position (i.e. the position A in FIG. 7A) for receiving specular reflection light, and define a position (i.e. the position B in FIG. 7A) displaced from the expected position by an aspecular angle, as a measuring position.

On the other hand, in the case where the multi-angle colorimeter 1 is tilted toward the normal G because of shake of the apparatus or a like movement, and the aperture plane X of the measurement aperture 3 is not in agreement with the measurement surface Sa of the object S to be measured, an expected position for receiving specular reflection light is not coincident with the actual position for receiving specular reflection light. For instance, a position where a peak value is obtained is shifted from the position A to the position A', as shown in FIG. 7B. In this case, if reflection light from the object S to be measured is received at the position B whose reference position is the position A, the position for receiving specular reflection light is displaced from the position B in FIG. 7A (corresponding to the position B' in FIG. 7B). As a result, an error may be generated in the output value to be obtained from the measurement light receiving sensor 23. In this example, a larger output value is obtained, as compared with the output value to be obtained in the arrangement shown in FIG. 7A.

Specifically, although specular reflection light is measured at the same light receiving angular position, the output values of the received reflection light are different from each other. In view of this, it is required to detect that the multi-angle colorimeter 1 has erroneously measured a position different from the position to be measured in the intensity distribution M (or M') due to shake. In this embodiment, the multi-angle colorimeter 1 is configured in such a manner that the shake detection light receiving sensor 32 disposed at the position in specular reflection direction is operable to monitor the protruding portion (corresponding to a portion having a peak value i.e. a specular reflection light component or a portion having a large degree of glossiness), which is presumed to be a proper portion for accurately detecting a change in the measuring position, in other words, reflection light in specular reflection direction. The other portion corresponding to a diffused light component (i.e. a portion having a small degree of glossiness) in the intensity distribution M (M') receives substantially the same level of the intensity (i.e. substantially the same level of the light amount) with respect to different light receiving positions. Accordingly, a change in the light receiving amount (i.e. a change in the spectral intensity) cannot be judged at the portion corresponding to the diffused light component, and therefore, it is impossible to detect whether shake has occurred at the portion corresponding to the diffused light component.

Figure 6:
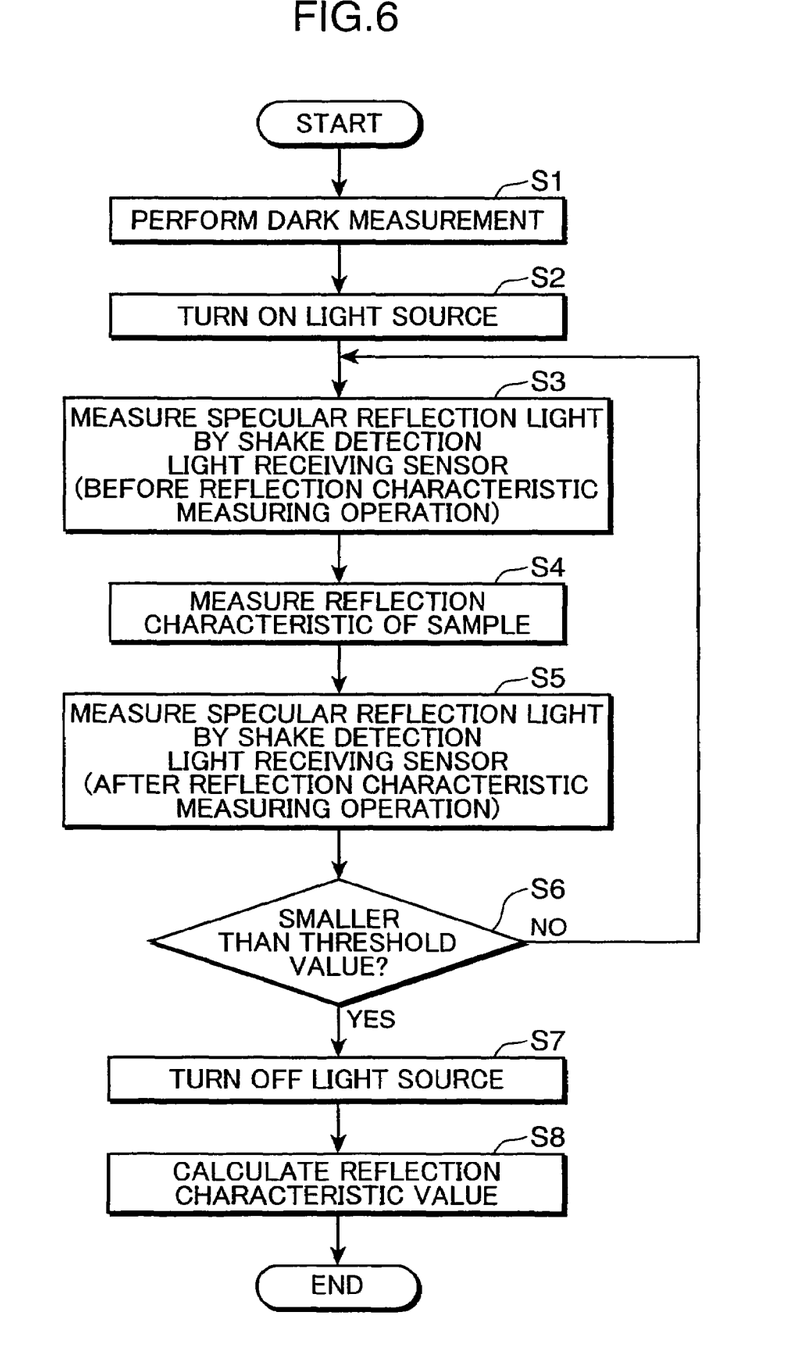
FIG. 6 is a flowchart showing a series of operations to be performed by a controlling section in the multi-angle colorimeter.

FIG. 6 is a flowchart showing a series of operations to be performed by the controlling section 40. As shown in FIG. 6, first, the controlling section 40 performs dark measurement (Step S1). Dark measurement is an operation of causing the measurement light receiving sensor 23 to perform a light receiving operation for obtaining an output value in a state that the light source 11 is turned off in order to cancel an offset (e.g. an output value to be obtained in a state that light incidence into the measurement light receiving sensor 23 is completely blocked) of various circuits in the measurement light receiving sensor 23 in the light receiving section 20 as a light receiving system, and the controlling section 40 or the like in a computation control system; or of various circuits in the shake detection light receiving sensor 32 in the light receiving system, and the controlling section 40 or the like in the computation control system. The output value (also called as a dark value) may be stored in an unillustrated storage in the controlling section 40. In the case where the respective parts of the multi-angle calorimeter 1 are in an electrically stable condition, the dark measurement may be omitted.

Subsequently, the illumination controller 41 controls the light source 11 to turn on (Step S2). Then, the shake detection light receiving sensor 32 is controlled by the shake detection controller 45 to measure a light amount in specular reflection direction i.e. a specular reflection light component. The measurement value i.e. a shake detection light receiving value is stored in e.g. a storage area such as an RAM in the controlling section 40 (Step S3). Then, the light receiving section 20 is controlled by the light receiving controller 42 and the driving controller 44 to measure a reflection characteristic of the object S to be measured. More specifically, first, after the light receiving section 20 is shifted to a predetermined initial position, the light receiving section 20 is sequentially shifted from the position for receiving specular reflection light to the respective light receiving angular positions of +15°, +25°, +45°, +75°, and +110° defined by e.g. the standard of the DIN (Deutsche Industrie Normenausschuss) by the driving controller 44, whereby reflection light is measured at each of the measuring positions (Step S4). Light receiving information (also called as a measurement light receiving value) to be obtained by the measuring operation is stored in e.g. the storage area in the controlling section 40 in the similar manner as described above. After the measuring operation at all the measuring positions is completed, the light receiving section 20 may be returned to the initial position.

Subsequently, the shake detection light receiving sensor 32 is controlled by the shake detection controller 45 to measure a light amount in a reflection direction i.e. a specular reflection light component. Similarly to Step S1, the measurement value i.e. a shake detection light receiving value is stored in the storage area in the controlling section 40 (Step S5). Then, the computation processor 43 compares the shake detection light receiving values measured at the timings before and after the reflection characteristic measuring operation (i.e. in Steps S3 and S5 before and after Step S4), which are stored in the storage area in the controlling section 40, in other words, performs a difference operation to calculate a difference; compares the calculated difference with a predetermined threshold value; and judges whether the difference is smaller than the threshold value. If it is judged that the difference is smaller than the threshold value (YES in Step S6), the routine proceeds to a termination process.

Specifically, when the routine enters the termination process, the illumination controller 41 controls the light source 11 to turn off (Step S7). Then, the computation processor 43 calculates a reflection characteristic value at each of the measuring positions, based on the measurement light receiving values outputted from the measurement light receiving sensor 23 (Step S8). In calculating the reflection characteristic value, the dark value obtained by the dark measurement, or other information necessary for calculating the reflection characteristic value e.g. a calibration coefficient may be used.

If, on the other hand, it is judged that the difference is not smaller than the threshold value (NO in Step S6), the routine returns to Step S3, and cyclically repeats the operations from Step S3 through S5 until it is judged that the difference is smaller than the threshold value. According to the flowchart shown in FIG. 6, the measuring operation by the shake detection light receiving sensor 32 is performed a smallest required number of times i.e. one time before the reflection characteristic measuring operation and one time after the reflection characteristic measuring operation. Actually, however, it is preferable to continue the measuring operation by the shake detection light receiving sensor 32 during a reflection characteristic measuring operation at each of the aspecular angles i.e. perform the measuring operation a certain number of times at a predetermined time interval, in other words, continue monitoring for shake detection. In the above arrangement, the amount of acquired data relating to shake detection light receiving values is increased. However, an increased amount of data enhances precision in shake detection, thereby enabling to accurately measure the reflection characteristic value of the object S to be measured.

As described above, the optical characteristic measuring apparatus (i.e. the multi-angle colorimeter 1) of the embodiment is an optical characteristic measuring apparatus for measuring an optical characteristic of an object to be measured (i.e. the object S to be measured). The optical characteristic measuring apparatus includes: an illuminating section (i.e. the illuminating section 10) for illuminating the object to be measured at a predetermined angle (i.e. the illumination angle α or the incident angle α); a measurement light receiving section (i.e. the light receiving section 20) for receiving reflection light from the object to be measured illuminated by the illuminating section to measure an optical characteristic; and a shake detection light receiving section (i.e. the shake detecting section 30) for receiving a specular reflection light component (e.g. the peak portion in the intensity distribution M of reflection light shown in FIG. 7A) in the reflection light from the object to be measured to detect shake of the apparatus.

The above arrangement enables to perform measurement without the need of providing a mechanical switch or a like device, and without depending on the shape of the object to be measured. The above arrangement also enables to detect whether shake of the apparatus has occurred during a period of receiving reflection light by the measurement light receiving section i.e. during an optical characteristic measuring operation, based on a light receiving value of the specular reflection light component to be obtained by the shake detection light receiving section. Thereby, the optical characteristic can be precisely measured with use of e.g. a light receiving value to be obtained by the measurement light receiving section, in the case where shake has not been detected.

In the above arrangement, the specular reflection light component is received in view of the following advantage. The specular reflection light component corresponds to a peak value (i.e. the peak portion) in the reflection light, and a significantly large light amount is obtained from the peak portion. The specular reflection direction or the vicinity of the specular reflection direction corresponds to a light receiving area where the light amount is greatly varied in response to a slight change of the light receiving angle. In this arrangement, even a slight shake of the apparatus can be detected by detecting a time-based variation in the peak value, which indicates that the apparatus is tilted with respect to the object to be measured due to the shake. A diffused light component in the reflection light other than the specular reflection light component does not cause a significantly large change in the light receiving value, even if shake has occurred. Accordingly, it is difficult to detect whether the apparatus is tilted or not, based on the diffused light component. The arrangement of the embodiment is advantageous in detecting erroneous measurement by shake of the apparatus, thereby enabling to perform measurement with improved reproducibility.

As described above, the embodiment of the invention employs a method for detecting shake of the apparatus by monitoring a variation in the light amount. This enables to eliminate the need of a mechanical switch or a like member, and mechanical adjustment. For instance, adjustment of the apparatus is completed by changing a threshold value. This enables to simplify the production process of the apparatus. Also, since the threshold value is changeable after the measuring apparatus as a measuring system is assembled, the magnitude of sensitivity with respect to shake of the apparatus can be easily changed. Further, since a mechanical arrangement is not provided in the measuring system, the occurrence rate of failure or malfunction of the measuring system is reduced, thereby enabling to enhance reliability of the measuring system.

In the above arrangement, preferably, the shake detection light receiving section includes a light receiving sensor (i.e. the shake detection light receiving sensor 32), and the light receiving sensor is arranged at a position in the vicinity of a light receiving direction corresponding to a specular reflection angle with respect to an illuminating direction corresponding to the predetermined angle defined by the illuminating section.

The above arrangement enables to perform shake detection with a simplified arrangement that the light receiving sensor is arranged at the position in the vicinity of the light receiving direction corresponding to the specular reflection angle.

In the above arrangement, preferably, a first computing section (i.e. the controlling section 40 or the computation processor 43) performs a computation of obtaining a time-based variation (i.e. a variation amount in light amount e.g. a difference of the aforementioned shake detection light receiving value) in the specular reflection light component, based on a light receiving value obtained by receiving the specular reflection light component by the shake detection light receiving section.

The above arrangement enables to easily judge or detect whether shake has occurred, based on the time-based variation (i.e. a change amount e.g. an amount indicating a change in light amount or light intensity from an initial value e.g. the shake detection light receiving value obtained before a measuring operation is started) in the specular reflection light component.

In the above arrangement, preferably, exclusively in the case where a value of the time-based variation during a period of receiving the reflection light by the measurement light receiving section is in a predetermined threshold value range, a second computing section (i.e. the controlling section 40 or the computation processor 43) performs a computation of obtaining the optical characteristic based on a light receiving value obtained by the measurement light receiving section.

The above arrangement enables to precisely obtain the optical characteristic by using the light receiving value to be obtained by the measurement light receiving section in the case where shake of the apparatus has not been detected, or shake of the apparatus has such a small magnitude that a time-based variation value is smaller than a predetermined threshold value.

In the above arrangement, preferably, the measurement light receiving section is pivotally rotatable about an axis which is orthogonal to a geometric plane including an optical axis of incident light incident onto the object to be measured, and an optical axis of the reflection light from the object to be measured, and which passes an intersect of the optical axis of the incident light and the optical axis of the reflection light.

The above arrangement enables to perform precise multi-angle measurement of illuminating in a single direction and receiving in multiple directions, while pivotally rotating the measurement light receiving section, in cooperation with the aforementioned shake detection.

The specification discloses the aforementioned arrangements. The following is a summary of the primary features of the arrangements.

An optical characteristic measuring apparatus according to an aspect of the invention includes: an illuminating section for illuminating an object to be measured at a predetermined angle; a measurement light receiving section for receiving reflection light from the object to be measured illuminated by the illuminating section to measure an optical characteristic of the object to be measured; a shake detection light receiving section for receiving a specular reflection light component in the reflection light from the object to be measured; and a shake detecting section for detecting a shake of the optical characteristic measuring apparatus based on an output from the shake detection light receiving section.

In the above arrangement, the optical characteristic measuring apparatus includes the illuminating section, the measurement light receiving section, and the shake detection light receiving section. The above arrangement enables to perform measurement without the need of providing a mechanical switch or a like device, and without depending on the shape of the object to be measured. The above arrangement also enables to detect whether shake of the apparatus has occurred during a period of receiving the reflection light by the measurement light receiving section i.e. during an optical characteristic measuring operation, based on a light receiving value of the specular reflection light component to be obtained by the shake detection light receiving section. Thereby, the optical characteristic can be precisely measured with use of e.g. a light receiving value to be obtained by the measurement light receiving section, in the case where shake has not been detected.

In the above arrangement, the specular reflection light component is received in view of the following advantage. The specular reflection light component corresponds to a peak value in the reflection light, and even a slight shake of the apparatus can be detected by detecting a time-based variation in the peak value, which indicates that the apparatus is tilted with respect to the object to be measured due to the shake.

Preferably, the shake detection light receiving section may include a light receiving sensor, and the light receiving sensor may be arranged at a position in the vicinity of a light receiving direction corresponding to a specular reflection angle with respect to an illuminating direction corresponding to the predetermined angle defined by the illuminating section.

In the above arrangement, shake detection can be performed with a simplified arrangement that the light receiving sensor is arranged at the position in the vicinity of the light receiving direction corresponding to the specular reflection angle.

Preferably, the shake detecting section may include a first computing section for obtaining a time-based variation in the specular reflection light component, based on a light receiving value obtained by receiving the specular reflection light component by the shake detection light receiving section.

The above arrangement enables to easily judge or detect whether shake has occurred, based on the time-based variation i.e. a change amount in the specular reflection light component obtained by the first computing section.

Preferably, the optical characteristic measuring apparatus may further include a second computing section for obtaining the optical characteristic based on a light receiving value obtained by the measurement light receiving section, exclusively in the case where a value of the time-based variation during a period of receiving the reflection light by the measurement light receiving section is in a predetermined threshold value range.

In the above arrangement, the optical characteristic can be precisely obtained by using the light receiving value to be obtained by the measurement light receiving section in the case where shake of the apparatus has not been detected, or shake of the apparatus has such a small magnitude that a time-based variation value is smaller than a predetermined threshold value.

Preferably, the measurement light receiving section may be pivotally rotatable about an axis which is orthogonal to a geometric plane including an optical axis of incident light incident onto the object to be measured, and an optical axis of the reflection light from the object to be measured, and which passes an intersect of the optical axis of the incident light and the optical axis of the reflection light.

In the above arrangement, the reflection light can be easily received in multiple directions while pivotally rotating the measurement light receiving section. This enables to perform precise multi-angle measurement of illuminating in a single direction and receiving in multiple directions in cooperation with the aforementioned shake detection.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An optical characteristic measuring apparatus comprising:
   an illuminating section for illuminating an object to be measured at a predetermined angle;
   a measurement light receiving section for receiving reflection light from the object to be measured illuminated by the illuminating section to measure an optical characteristic of the object to be measured;
   a shake detection light receiving section for receiving a specular reflection light component in the reflection light from the object to be measured; and
   a shake detecting section for detecting a shake of the optical characteristic measuring apparatus based on an output from the shake detection light receiving section.

2. The optical characteristic measuring apparatus according to claim 1, wherein
   the shake detection light receiving section includes a light receiving sensor, and
   the light receiving sensor is arranged at a position in the vicinity of a light receiving direction corresponding to a specular reflection angle with respect to an illuminating direction corresponding to the predetermined angle defined by the illuminating section.

3. The optical characteristic measuring apparatus according to claim 1, wherein
   the shake detecting section includes a first computing section for obtaining a time-based variation in the specular reflection light component, based on a light receiving value obtained by receiving the specular reflection light component by the shake detection light receiving section.

4. The optical characteristic measuring apparatus according to claim 3, further comprising:
   a second computing section for obtaining the optical characteristic based on a light receiving value obtained by the measurement light receiving section, exclusively in the case where a value of the time-based variation during a period of receiving the reflection light by the measurement light receiving section is in a predetermined threshold value range.

5. The optical characteristic measuring apparatus according to claim 1, wherein
   the measurement light receiving section is pivotally rotatable about an axis which is orthogonal to a geometric plane including an optical axis of incident light incident onto the object to be measured, and an optical axis of the reflection light from the object to be measured, and which passes an intersect of the optical axis of the incident light and the optical axis of the reflection light.

* * * * *